United States Patent [19]
Besterman et al.

[11] Patent Number: 6,100,273
[45] Date of Patent: *Aug. 8, 2000

[54] WATER SOLUBLE CAMPTOTHECIN DERIVATIVES

[75] Inventors: Jeffrey Mark Besterman, Durham; Michael Glenn Evans, Pittsboro; Karen Elizabeth Lackey, Durham; Michael Joseph Luzzio, Durham; Michael Robert Peel, Durham; Daniel David Sternbach, Chapel Hill, all of N.C.

[73] Assignee: Glaxo Wellcome Inc., Research Triangle Park, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/977,217

[22] Filed: Nov. 24, 1997

Related U.S. Application Data

[63] Continuation of application No. 08/432,134, filed as application No. PCT/US93/10987, Nov. 10, 1993, abandoned, which is a continuation of application No. 07/975,363, Nov. 12, 1992, abandoned, which is a continuation of application No. 07/975,364, Nov. 12, 1992, abandoned.

[51] Int. Cl.$^7$ ..................... A61K 31/4745; C07D 491/22

[52] U.S. Cl. ............................. 514/279; 514/81; 546/23; 546/41

[58] Field of Search ................................. 546/41, 48, 23; 514/279, 81

[56] References Cited

U.S. PATENT DOCUMENTS

| | | | |
|---|---|---|---|
| 4,399,276 | 8/1983 | Miyasaka et al. | 546/48 |
| 4,399,282 | 8/1983 | Miyasaka et al. | 546/48 |
| 4,604,463 | 8/1986 | Mijasaka et al. | 544/125 |
| 4,894,456 | 1/1990 | Wall et al. | 546/41 |
| 4,943,579 | 7/1990 | Vishnuvajjala et al. | 514/283 |
| 5,061,800 | 10/1991 | Yaegashi et al. | 546/48 |
| 5,126,351 | 6/1992 | Luzzio et al. | 514/297 |
| 5,342,947 | 8/1994 | Lackey et al. | 546/41 |
| 5,559,235 | 9/1996 | Luzzio et al. | 546/41 |

FOREIGN PATENT DOCUMENTS

| | | |
|---|---|---|
| 0321122 | 6/1989 | European Pat. Off. . |
| 0471358 | 2/1992 | European Pat. Off. . |
| 540 099 A1 | 5/1993 | European Pat. Off. . |
| 556 585 A2 | 8/1993 | European Pat. Off. . |
| wO 9205785 | 4/1992 | WIPO . |
| 94-11377 | 5/1994 | WIPO . |

OTHER PUBLICATIONS

Burger, Ed. "Medicinal Chemistry" 2d Ed. Interscience, NY, 1960 p. 42.

Wall et al., "Plant Antitumor Agents. I. The Isolation and Structure of Camptothecin . . . " JACS, 88/16 (Aug. 20, 1966) 3888–3890.

Liu, "DNA Topoisomerases–Enzymes . . . , " CRC Critical Review in Biochem., 15, 1–24 (1983).

Vosberg, "DNA Topoisomerases: Enzymes taht . . . , " Current Topics in Microbiology and Emmunology, 19–102 (1985).

Schultz, "Camptothecin," Chem. Rev., 73, (1973) 385–405.

Muggia, "Phase 1 Clinical Trial of Weekly . . . , " Cancer Chemotherapy Reports Part 1, 56 (1972) 515–521.

Wani et al., Plant Antitumor Agents. 18. I. Synthesis . . . , J. Med. Chem., 23 (1980) 554–560.

Giovanella et al. "Correlation Between Response to . . . ," Cancer, 52: 1146–1152 (1983).

Boven et al., "The Nude Mouse in Oncology Research," CRC Press, Inc., Boca Raton, FL (1991) 305–316.

(List continued on next page.)

*Primary Examiner*—Richard L. Raymond
*Attorney, Agent, or Firm*—John L. Lemanowicz

[57] ABSTRACT

The present invention relates to water soluble, camptothecin derivatives of formula (I).

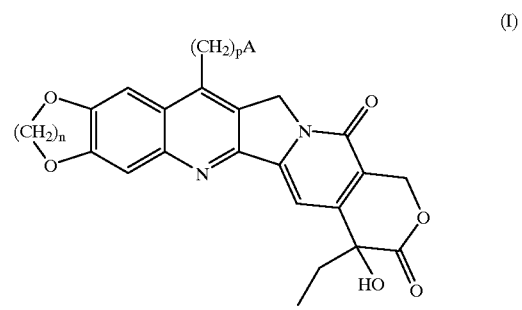

(I)

wherein A represents a moiety of the formula (IIA), (IIB) or (IIC):

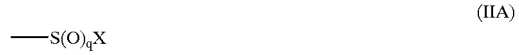

(IIA)

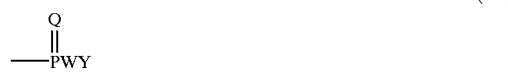

(IIB)

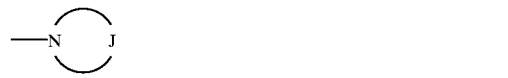

(IIC)

X is selected from the group consisting of alkyl, aryl, $(CH_2)_mOR^1$, $(CH_2)_mSR^1$ and $(CH_2)_mNR^1R^2$ wherein m is an integer of 0 to 6, and $R^1$ and $R^2$ are hydrogen, lower alkyl, aryl or together with the nitrogen form a 5–7 membered ring; q is an integer of 0 to 2; n represents the integer 1 or 2; p is an integer of 1 to 6; Y and W are selected from the group consisting of alkyl, aryl, alkoxy, aryloxy and amino, Q is oxygen or sulfur; P is phosphorus; J represents the atoms necessary to complete a 5 or 6 membered aromatic ring; and the pharmaceutically acceptable salts thereof; their use as topoisomerase inhibitors, their preparation; and their use in the treatment of cancer.

28 Claims, No Drawings

OTHER PUBLICATIONS

Sawada et al., "Chemical Modification of an Antitumor . . . ," Chem. Pharm. Bull. 39 (1991) 2574–2580.

Sawada et al., "Synthesis and Antitumor Activity . . . ," Chem. Pharm. Bull. 39 (1991), 3183–3188.

Wani et al. "Plant Antitumor Agents. 23. I. Synthesis . . . ," J. Med. Chem., 29 (1986) 2358–2363.

Wani et al. "Plant Antitumor Agents. 25.I.. Total . . . ," J. Med. Chem., 30 (1987) 1774–1779.

Hertzberg et al., "Modification of the Hydroxy Lactone . . . ," J. Med. Chem., 32 (1989) 715–720.

Kingsbury et al., "Synthesis of Water–Soluble (Aminoalkyl) Camptothecin . . . ," J. Med. Chem., 34 (1991) 98–107.

Ejima et al., "Antitumor Agents. VI. Synthesis . . . ," Chem. Pharm. Bull., 40 (1992) 683–688.

Abbott, "Bioassay of Plant Extracts For Anticancer Activity," Cancer Treatment Reports, vol. 80, No. 8, 1007–1010 (1976).

Baumgarten et al., Naphthyridines I Synthesis of Some 1,7–Naphthyridines, JACS, 77 2438–2440 (1955).

Borch et al., "A New Method for the Methylation of Amines," J. Org. Chem., vol. 37, No. 10, 1673–1674 (1972).

Fiebig, "Comparison of Tumor Response in Nude Mice and in Plants," ESO Momographs, Heidleburg, 25–30 (1988).

WATER SOLUBLE CAMPTOTHECIN DERIVATIVES

This application is a Continuation of U.S. application Ser. No. 08/432,134 filed May 9, 1995, abandoned, which is a 371 application of PCT/US93/10987 filed Nov. 10, 1993 which is a continuation of U.S. application Ser. No. 07/975,363 filed Nov. 12, 1992, abandoned and U.S. application Ser. No. 07/975,364 filed Nov. 12, 1992, abandoned.

The present invention relates to water soluble, camptothecin derivatives which are substituted in the 7 position; the invention also relates to the use of these compounds as topoisomerase inhibitors in the treatment of tumors and to methods of their preparation.

BACKGROUND OF THE INVENTION

Camptothecin, a natural, cytotoxic alkaloid, is a topoisomerase I inhibitor and potent antitumor agent. It was first isolated from the leaves and bark of the Chinese plant, *Camptotheca accuminata*, by Wall, et al. (J. Am. Chem. Soc., 88 3888 (1966)).

As depicted, camptothecin is a fused ring system composed of a quinoline (A and B), fused to a pyrrolidine ring (C), fused to an alpha-pyridone ring (D) which in turn is fused to a lactone ring (E).

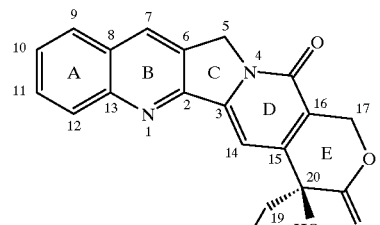

CAMPTOTHECIN

It has an asymmetric carbon at the 20 position making two enantiomeric forms possible. However, the naturally occurring compound is found in the "S" configuration as shown above.

Cytotoxic agents are often employed to control or eradicate tumors i.e., they are chemotherapeutic agents. Camptothecin's cytotoxic activity is thought to be directly related to camptothecin's potency as a topoisomerase inhibitor. [For detailed explanations of the topoisomerase function see A. Lehninger, *Principles of Biochemistry*, 813, Worth Publishers, New York (1982); L. F. Liu, "DNA Topoisomerases," *CRC Critical Review in Biochemistry*, 1–24, 15 (1983); and H. Vosberg, "DNA Topoisomerases: Enzymes that Control DNA Conformation," *Current Topics in Microbiology and Immunology*, 19, Springer-Verlag, Berlin (1985).] In particular, camptothecin has been shown to be effective in the treatment of leukemia (L-1210) and certain solid tumors in laboratory animals, e.g., see DNA Topoisomerases in Cancer, Potmesil, M. et al., Oxford Univ. Press (1991), Chem. Rev. 23, 385 (1973) and Cancer Treat. Rep., 60, 1007 (1967).

Unfortunately, in the clinic camptothecin's promise as an effective antitumor agent has not been completely fulfilled. Camptothecin is essentially insoluble in physiologically compatible, aqueous media, and must be modified to make it sufficiently soluble for parenteral administration, a preferred mode for antitumor treatment. It can be made soluble by forming its sodium salt, that is, by opening the lactone with sodium hydroxide (see F. M. Muggia, et al., *Cancer Chemotherapy Reports*, pt. 1, 56, No.4, 515 (1972)).

However, M. C. Wani, et al., *J. Med. Chem,* 23, 554 (1980), reported that the alpha-hydroxy lactone moiety of ring E is an absolute requirement for antitumor activity.

In the art there are examples of modifications and derivatives of camptothecin prepared to improve its solubility in water. Although many of these derivatives were active in in vitro and in early animal studies using leukemia (L-1210) models, they were disappointing in chronic, animal models involving implanted solid tumors.

Miyasaka, et al., U.S. Pat. No. 4,399,282, discloses a group of camptothecin derivatives substituted at the 7 position with, inter alia, hydroxymethyl and alkoxymethyl. Further, Miyasaka, et. al. in U.S. Pat. No. 4,399,276 discloses camptothecin-7-aldehyde and certain related aldehyde derivatives such as acetals, oximes and hydrazones. More recently, Vishnuvajjala, et al., in U.S. Pat. No. 4,943,579, claimed a series of water-soluble camptothecin derivatives with substituents on the A ring as does Boehm, et al., European Patent Application 0 321 122 A2. Other examples of derivatives of camptothecin include Miyasaka, et al., U.S. Pat. No. 4,473,692 and No. 4,545,880; and W. Kingsbury, et al., *J. Med. Chem.*, 34, 98 (1991). None of these references reported compounds with antitumor activity greater than that of camptothecin itself.

Wani and co-workers reported that 10,11-methylenedioxycamptothecin is more potent than unsubstituted camptothecin (see M. C. Wani, et al., *J. Med. Chem,* 29, 2358 (1986) and 30, 2317 (1987)). However, its water solubility is as poor as camptothecin which seriously limits its clinical utility.

We have now found water-soluble analogs of camptothecin with good, topoisomerase I inhibitory activity in vitro, and impressive, antitumor activity in vivo.

SUMMARY OF THE INVENTION

One aspect of the present invention is water-soluble camptothecin derivatives of formula (I),

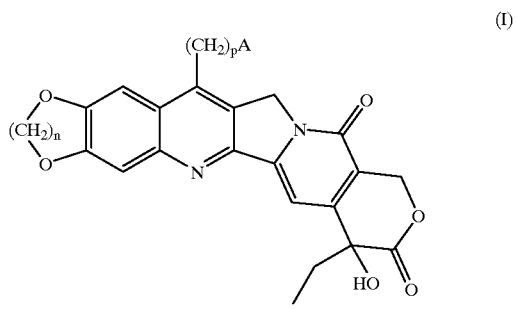

(I)

wherein A represents a moiety of the formula (IIA), (IIB) or (IIC):

(IIA)

(IIB)

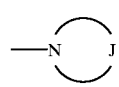

(IIC)

X is selected from the group consisting of alkyl, aryl, $(CH_2)_m OR^1$, $(CH_2)_m SR^1$ and $(CH_2)_m NR^1 R^2$ wherein m is an integer of 0 to 6, and $R^1$ and $R^2$ are hydrogen, lower alkyl, aryl or together with the nitrogen form a 5–7 membered ring; q is an integer of 0 to 2; n represents the integer 1 or 2; p is an integer of 1 to 6; Y and W are selected from the group consisting of alkyl, aryl, alkoxy, aryloxy and amino, Q is oxygen or sulfur; P is phosphorus; J represents the atoms necessary to complete a 5 or 6 membered aromatic ring; and the pharmaceutically acceptable salts thereof.

The term "alkyl" as used herein and with respect to the alkyl moiety in any other substituent defined herein such as "alkoxy" means a straight chain, branched chain or cyclic alkyl group having 1 to 6 carbon atoms. The term "lower alkyl" more specifically refers to an alkyl moiety containing 1 to 3 carbon atoms.

The term "aryl" as used herein and with respect to the aryl moiety in any other substituent defined herein such as "aryloxy" means phenyl, substituted phenyl such as anilino, and heteroaryl groups containing from 5 to 7 ring members such as pyrrolyl, pyrazolyl, imidazolyl, triazolyl, oxazolyl, isoxazolyl, oxadiazolyl, thiazolyl, isothiazolyl, thiadiazolyl, pyridyl, pyrazinyl, pyrimidinyl, pyridazinyl, triazinyl and tetrazinyl. Preferred aryl groups are selected from the group consisting of phenyl, pyridyl and pyrimidyl which may be unsubstituted or substituted. Examples of substituents which may be present on the aromatic ring include halogen (e.g., fluorine, chlorine, bromine or iodine), nitro, amino, dialkylamino, diphenylamino, alkyl, alkoxy, alkoxyalkyl, hydroxyalkyl, alkenyl, aryl (e.g., phenyl, pyridyl, etc.), alkylthioalkyl, aminoalkyl, —NHCOR$^1$ or —NHCO(CH$_2$)$_m$NR$^1$R$^2$ where $R^1$ and $R^2$ are defined as above. Preferred substituents include, for example nitro, amino, NHCO(CH$_2$)$_m$NR$^1$R$^2$ (e.g. —NHCOCH$_2$N(CH$_3$)$_2$) and NHCOR$^1$ (e.g. NHCOCH$_3$). More specific examples of aryl groups are phenyl, pyridyl, pyrimidyl, anilino, nitrophenyl, acetamidophenyl and dimethylaminoacetamidophenyl.

Examples of rings formed by the combination of $R^1$ and $R^2$ groups and the nitrogen atom include aziridinyl, azetidinyl, pyrrolidinyl, piperidinyl, hexamethyleniminyl, imidazolidinyl, pyrazolidinyl, isoxazolidinyl, piperazinyl, N-methylpiperazinyl, homopiperazinyl, N-methylhomopiperazinyl, thiazolidinyl, isothiazolidinyl, morpholino or thiomorpholino.

The term "alkenyl" as used herein refers to straight chain or branched chain alkenyl groups having 3 to 7 carbon atoms.

Preferably X is selected from the group consisting of alkyl, aryl and (CH$_2$)$_m$NR$^1$R$^2$.

Preferably Q is oxygen and W and Y are both alkoxy.

Particular compounds of formula (I) are those wherein A is a moiety of formula (IIC) and J represents the atoms necessary to complete an aromatic ring selected from the group consisting of pyrazolyl, imidazolyl, triazolyl, oxazolyl, isoxazolyl, oxadiazolyl, thiazolyl, isothiazolyl, thiadiazolyl, pyridyl, pyrazinyl, pyrimidinyl, pyridazinyl, triazinyl and tetrazinyl. These rings may be unsubstituted or substituted. Representative substituents are described above. Preferred aromatic rings are selected from the group consisting of imidazolyl, pyridyl, pyridazinyl and pyrazinyl which may be unsubstituted or substituted. Preferred substituents include, for example, alkyl, (e.g., methyl, ethyl or propyl) and hydroxalkyl, (e.g. hydroxymethyl).

Those skilled in the art will readily appreciate that depending on the aromatic ring system, the compounds of the invention may be obtained as quaternary salts. Others can be converted to quaternary salts by reaction with alkylating agents such as methyl iodide, CH$_3$OSO$_2$F, etc. Quaternary salts, especially chloride salts are preferred.

Preferably p is an integer of 1, 2 or 3, especially 1.

Pharmaceutically acceptable salts include, but are not limited to salts with inorganic counterions such as chloride, sulfate, phosphate, diphosphate, bromide and nitrate or salts with an organic acid such as acetate, malate, maleate, fumarate, tartrate, succinate, citrate, lactate, methanesulfonate, p-toluenesulfonate, palmoate, salicylate and stearate. Other acids such as oxalic, while not in themselves pharmaceutically acceptable, may be useful as intermediates in obtaining the compounds of the invention and their pharmaceutically acceptable salts.

The lactone ring, ring E, may be opened by alkali metal or alkaline-earth metal bases, for example sodium hydroxide or calcium hydroxide, to form alkali metal or alkaline-earth metal salts of the corresponding open E ring form of the compounds of formula (I). Because of its better solubility in water, the open E ring form may advantageously be purified by conventional recrystallization techniques. Accordingly, said open E ring form may then be used as an intermediate to form the compounds of formula (I), for example by treatment with acid, e.g., hydrochloric acid, and thereby produce a purified form of the compounds of formula (I).

As noted above, the camptothecin moiety has an asymmetric carbon atom at the 20 position making two enantiomeric forms, i.e., "R" and "S" configurations, possible. This invention includes both enantiomeric forms and any combinations of these forms. For simplicity, where no specific configuration at the 20 position is depicted in the structural formulas, it is to be understood that both enantiomeric forms and mixtures thereof are represented. Unless noted otherwise, the nomenclature convention, "(R,S)", denotes a racemic (approximately equal portion) mixture of the R and S enantiomers while "(R)" and "(S)" denote essentially optically pure R and S enantiomers respectively. In certain cases, the sulfur atom is a chiral center and additional isomers are possible. This invention includes these enantiomers and combinations thereof as well. Also included in the invention are other forms of the compound of formula (I), such as solvates, hydrates, polymorphs and the like.

Another aspect of the invention is a method of inhibiting topoisomerase Type I in mammalian cells comprising administering to a patient a topoisomerase inhibiting amount of a compound of formula (I), and a method of treating a tumor in a mammal comprising administering to a mammal bearing a tumor, an effective antitumor amount of a compound of formula (I). A further aspect comprises pharmaceutical formulations containing a compound of formula (I) as an active ingredient. Methods of preparation of the compounds of formula (I) and the associated novel chemical intermediates used in the synthesis, as taught herein, are also within the scope of the present invention.

DETAILED DESCRIPTION OF THE INVENTION

Specific compounds of formula (I) include:

7-Methylthiomethyl-10,11 -(ethylenedioxy)-20(S)-camptothecin;

7-Methylthiomethyl-10,11 -(methylenedioxy)-20(S)-camptothecin;

7-(2-Pyridylthio)methyl-10,11-(ethylenedioxy)-20(S)-camptothecin;

7-(2-Pyridylthio)methyl-10,11-(methylenedioxy)-20(S)-camptothecin;

7-(2-Pyrimidylthio)methyl-10,11-(methylenedioxy)-20(S)-camptothecin;

7-(4-Nitrophenylthio)methyl-10,11-(methylenedioxy)-20(S)-camptothecin;

7-(4-Acetamidophenylthio)methyl-10,11-(methylenedioxy)-20(S)-camptothecin;
7-Methylsulfinylmethyl-10,11-(ethylenedioxy)-20(S)-camptothecin;
7-Methylsulfinylmethyl-10,11-(methylenedioxy)-20(S)-camptothecin;
7-(2-Pyridylsulfinyl)methyl-10,11-(methylenedioxy)-20(S)-camptothecin;
7-Methylsulfonylmethyl-10,11-(ethylenedioxy)-20(S)-camptothecin;
7-Methylsulfonylmethyl-10,11-(methylenedioxy)-20(S)-camptothecin;
7-Dimethylphosphonomethylene-10,11 (methylenedioxy)-20(S)-camptothecin;
7-Dimethylphosphonomethylene-10,11-(ethylenedioxy)-20(S)-camptothecin;
7-Di-n-butylphosphonomethylene-10,11-(ethylenedioxy)-20(S)-camptothecin;
7-(4-Aminophenylthio)methyl-10,11-(methylenedioxy)-20(S)-camptothecin;
7-(4-Acetamidophenylthio)methyl-10,11-(ethylenedioxy)-20(S)-camptothecin;
7-(4-Aminophenylthio)methyl-10,11-(ethylenedioxy)-20(S)-camptothecin;
7-(2-Aminoethylthio)methyl-10,11-(ethylenedioxy)-20(S)-camptothecin;
7-(2-Dimethylaminoethylthio)methyl-10,11-(ethylenedioxy)-20(S)-camptothecin;
7-(3-Aminopropylthio)methyl-10,11-(ethylenedioxy)-20(S)-camptothecin;
7-(3-Dimethylaminopropylthio)methyl-10,11-(ethylenedioxy)-20(S)-camptothecin;
7-(2-Methylaminoethylthio)methyl-10,11-(ethylenedioxy)-20(S)-camptothecin;
7-(2-Aminoethylthio)methyl-10,11-(methylenedioxy)-20(S)-camptothecin;
7-(2-Methylaminoethylsulfinyl)methyl-10,11-(ethylenedioxy)-20(S)-camptothecin;
7-(3-Aminopropylsulfinyl)methyl-10,11-(ethylenedioxy)-20(S)-camptothecin;
7-(3-Dimethylaminopropylsulfinyl)methyl-10,11-(ethylenedioxy)-20(S)-camptothecin;
7-(4-(2-Dimethylaminoacetamido)phenylthio)methyl-10,11-(ethylenedioxy)-20(S)-camptothecin;
7-Pyridinium methylene-10,11-methylenedioxy-20(S)-camptothecin;
7-Pyridinium methylene-10,11-ethylenedioxy-20(S)-camptothecin;
7-Pyridinium methylene-10,11-ethylenedioxy-20(R,S)-camptothecin;
7-(3'-Methylimidazolium)methylene-10,11-ethylenedioxy-20(S)-camptothecin;
7-(3'-Methylimidazolium)methylene-10,11-methylenedioxy-20(S)-camptothecin;
7-Pyridazinium methylene-10,11-methylenedioxy-20(S)-camptothecin;
7-Pyridazinium methylene-10,11-ethylenedioxy-20(S)-camptothecin;
7-(3'-Hydroxymethylpyridinium)methylene-10,11-ethylenedioxy-20(S)-camptothecin;
7-(3'-Hydroxymethylpyridinium)methylene-10,11-methylene-dioxy-20(S)-camptothecin;
7-Pyrazinium methylene-10,11-ethylenedioxy-20(S)-camptothecin;
7-Pyrazinium methylene-10,11-methylenedioxy-20(S)-camptothecin;
7-Imidazol-1-ylmethylene-10,11-methylenedioxy-20(S)-camptothecin;
7-Imidazol-1-ylmethylene-10,11-ethylenedioxy-20(S)-camptothecin;
7-(4'-Hydroxymethylpyridinium)methylene-10,11-ethylenedioxy-20(S) camptothecin;
and pharmaceutically acceptable salts thereof.

According to one general process (A), the compounds of formula (I) wherein A is —SX or a protected derivative thereof (e.g. intermediates of the formula (IB) shown in Scheme III below) may be prepared by the procedure shown in Step 2 of Scheme I.

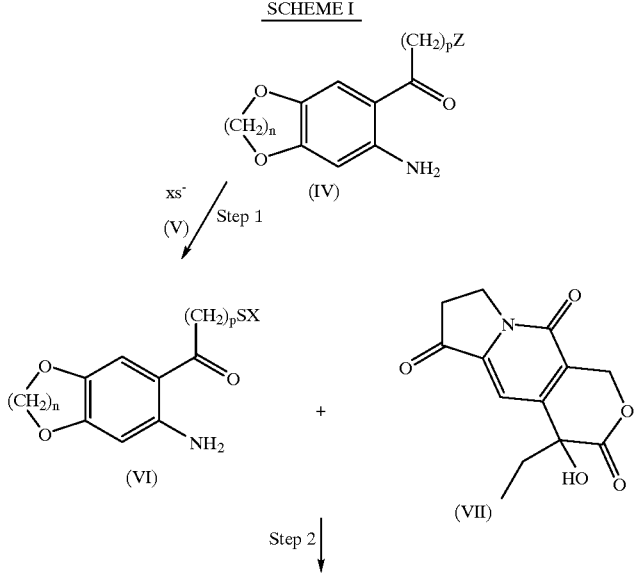

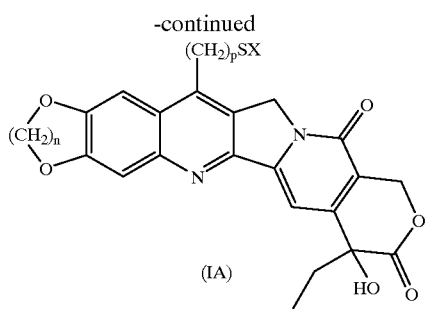

(IA)

In Step 1, a compound of formula (IV) is reacted with a compound of formula (V) to yield a compound of formula (VI), wherein X is alkyl, aryl (e.g., anilino), $(CH_2)_mOR^1$, $(CH_2)_mSR^1$, or $(CH_2)_mNR^1R^2$ or a protected derivative thereof (e.g. N-benzyloxycarbonyl-2-aminoethyl) by displacement of the leaving group, Z, (as defined in J. March, *Advanced Organic Chemistry*, 3rd. Ed., page 179, John Wiley & Sons, New York (1985)), for example, a halogen, e.g., chloro. This displacement reaction is conducted in a well-known manner and conveniently carried out in a solvent system, for example, a (C1-4) alkanol, a (C2-4) alkylene diol, 1-hydroxy-2-methoxyethane, dimethyacetamide (DMAC), N-methylpyrrolidinone, dimethyl formamide (DMF), tetrahydrofuran (THF), dimethyl sulfoxide (DMSO), toluene or a combination of these solvents in the presence of excess compound of formula (V) (mercaptan), with or without a base, e.g., sodium hydride or cesium carbonate.

In Step 2 (General Process A), compound of formula (VI) is reacted with a tricyclic ketone of formula (VII). This reaction can be carried out according to the method taught in U.S. Pat. No. 4,894,456 (hereinafter, '456), issued Jan. 16, 1990 to Wall et al., incorporated herein by reference, to yield a compound of formula (IA).

The reaction is preferably carried out in the presence of an acid or base catalyst. The acid catalyst is preferably a mineral acid such as for example HCl, $H_2SO_4$, $HNO_3$ and $H_3PO_4$ or an organic acid such as $C_{1-8}$ alkanoic acids and $C_{1-12}$ arylsulfonic acids, especially p-toluenesulfonic acid. The base catalyst is preferably an inorganic base such as for example sodium and potassium carbonate and sodium and potassium bicarbonate or an organic base such as a hindered base for example triethylamine and diisopropylamine.

The reaction may be carried out neat or in the presence of a polar or non-polar solvent. Preferred polar solvents are the $C_{1-6}$ alcohols, ethers and dimethylformamide. Preferred non-polar solvents are branched or staight chained alkyl hydrocarbons having 4–10 carbon atoms and aromatic hydrocarbons having 6–20 carbon atoms, especially toluene. The reaction is generally conducted with heating at reflux.

The compounds of formula (IV) may be prepared according to the procedure shown in Scheme II.

SCHEME II

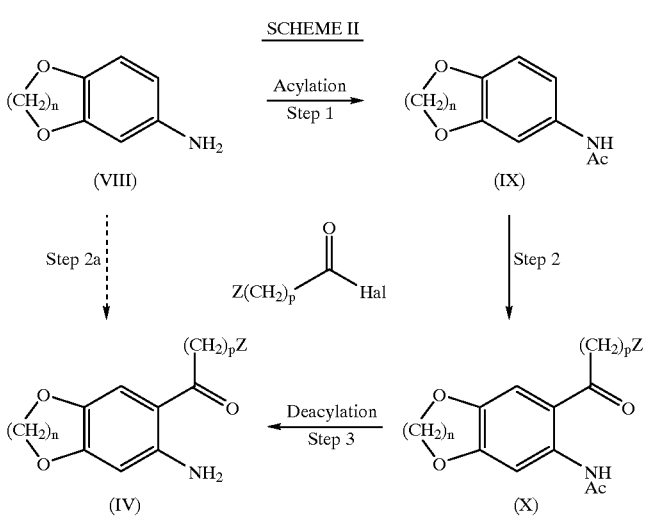

In Step 1 of Scheme II, a compound of formula (VIII) is reacted with an acylating agent, for example, a (C2-5) alkanoic acid halide or (C2-5) alkanoic acid anhydride, e.g., acetyl chloride or acetic anhydride, in the presence of a weak base, for example, potassium carbonate, in a polar, aprotic, solvent, for example, chloroform, to yield a compound of formula (IX), wherein Ac is a (C2-5) acyl group.

In Step 2, a compound of formula (IX) is reacted with an acid halide of formula (XI), wherein Z is a leaving group as defined above and Hal is halogen, in the presence of a metallic halide, e.g., zinc chloride, in a polar, aprotic solvent, e.g., nitromethane, to yield a compound of formula (X). A compound of formula (XI), for example, may be a haloacetyl halide, e.g., chloroacetyl chloride, or a haloacetonitrile, e.g., chloroacetonitrile.

In Step 3, a compound of formula (IV) is formed by removal of the acyl group, Ac, from a compound of formula (X), i.e., deacylation, by methods known in the art, such as those taught in T. Green, *Protective Groups in Organic Chemistry*, Chap. 7, John Wiley, New York (1981). For example, a compound of formula (X) may be heated at reflux in concentrated hydrochloric acid, and the resulting salt neutralized with a base, e.g., sodium hydroxide, to yield a compound of formula (IV).

When the compound of formula (VIII) is the ethylenedioxy compound, i.e., n is equal to 2, it may be reacted directly with a compound of formula (XI), without first protecting the amino group by acylation, to yield directly the corresponding compound of formula (IV).

Alternatively compounds of formula (IV) may be prepared according to the method taught by T. Sugasawa, et al., *J. Org. Chem.*, 44, 578 (1979).

The compounds of formula (VI) are novel and constitute another manifestation of the invention. Typical examples of the compound of formula (VI) are: 1-methylthio-[2'-amino-4'5'-(ethylenedioxy)]acetophenone, 1-methylthio-[2'-amino-4'5'-(methylenedioxy)]acetophenone, 1-(2-pyridylthio)-[2'-amino-4'5'-(ethylenedioxy)]acetophenone, 1-(2-pyridylthio)-[2'-amino-4'5'-(methylenedioxy)]acetophenone, 1-(4-pyridylthio)-[2'-amino-4'5'-(ethylenedioxy)]acetophenone, 1-(4-pyridylthio)-[2'-amino-4'5'-(methylenedioxy)]acetophenone, 1-(2-pyrimidinylthio)-[2'-amino-4'5'-(methylenedioxy)]acetophenone, 1-(4-nitrophenyl-thio)-[2'-amino-4'5'-methylenedioxy)]acetophenone, 1-(4-acetamidophenylthio)-[2'-amino-4'5'-(methylenedioxy)]acetophenone, 1-(4-acetamidophenylthio)-[2'-amino-4'5'-(ethylenedioxy)]acetophenone, and 1-[(N-benzyloxycarbonyl)-2-aminoethylthio]-[2-amino-4'5'-(ethylenedioxy)]acetophenone.

The tricyclic ketone of formula (VII) may be prepared according to the procedure of Wall, et al., U.S. Pat. No. 4,894,456, at column 11, starting at line 30. It is apparent from Scheme I that the configuration of the asymmetric carbon of the compound of formula (VII) will govern the configuration of the compounds of formula (I). The racemic compound of formula (VII) can be resolved into either of its enantiomers by the method of Wani, et al., in U.S. Pat. No. 5,053,512, (hereinafter, "'512") incorporated herein by reference.

According to a further general process (B), compounds of formula (I) wherein A is $S(CH_2)_mNH_2$ may be prepared by hydrolysis of compounds of formula (IB) where Z* is a protective group (e.g., acyl group or an acyloxy group and, more particularly, a benzyloxycarbonyl group) as shown in Scheme III.

SCHEME III

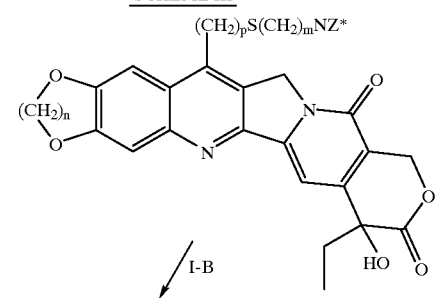

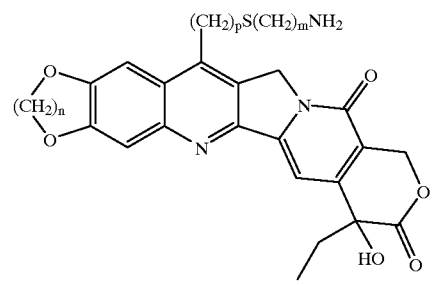

Hydrolysis conditions are selected to form the desired amine. Various hydrolysis procedures may be employed including aqueous trifluoroacetic acid, aqueous hydrochloric acid and other aqueous mineral or organic acids.

According to a further general process (C) compounds of the formula (I) wherein A is a moiety of formula (IIB) or (IIC) may be prepared by the procedure shown in Step 2 of Reaction Scheme IV in which compounds of the formula (XII) are reacted with a suitable nucleophile, for example a compound of formula (XIII)

RPWY            (XIII)

wherein R is a group of formula QR* and R* is a readily displaceable group, for example an alkyl or silyl group or a compound of formula (III)

(III)

to provide compounds of the formula (I) by displacement of the leaving group under conditions similar to those shown in Scheme I above or in a melt of the nucleophile.

SCHEME IV

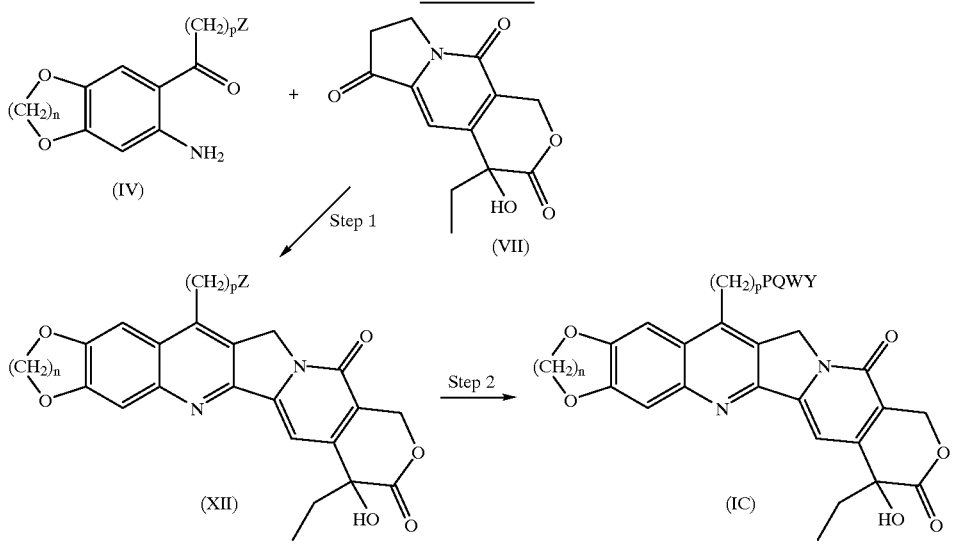

In one preferred embodiment of general process (C) compounds of formula (I) wherein W=Y=alkoxy or acyloxy and Q represents oxygen may be prepared by reaction of a compound of formula (XII) with a trialkyl or triacyl phosphate of formula $(RO)_3P$. In a further preferred embodiment of process (C) compounds of general formula (I) wherein A is a moiety of formula (IIC) may be prepared in a melt of the nucleophile.

Generally, the displacement reaction shown in Scheme IV, Step 2 provides low yields if the nucleophile is a moiety of formula (IIC) substituted at a position adjacent or ortho to the nitrogen atom.

The reaction of the compound of formula (IV) with the tricyclic ketone (VII) is described in Wall, et al. '456, supra.

According to another general process (D), a compound of formula (I) according to the invention may be converted into another compound of the invention using conventional procedures.

Thus, compounds of the formula (I) wherein A is —SOX and —$SO_2X$ may be prepared by oxidation of compounds of the formula (I) wherein A is —SX. Oxidation conditions may be selected to form the desired sulfinyl or sulfonyl derivative. Various oxidizing agents may be employed in the reactions including ozone, hydrogen peroxide/ acetic acid, peroxyacids, periodates, perborates, peroxy-sulfates, peroxides, hydroperoxides, iodine (III), permanganates, etc. Useful reaction conditions are illustrated in the Examples below.

A compound of formula (I) wherein one or more of $R^1$ and $R^2$ represents a hydrogen atom, may be alkylated using conventional techniques. The reaction may be effected using a suitable alkylating agent such as an alkyl halide, an alkyl tosylate or a dialkylsulphate. The alkylation reaction may conveniently be carried out in an organic solvent such as an amide, e.g. dimethylformamide, or an ether, e.g. tetrahydrofuran, preferably in the presence of a base. Suitable bases include, for example, alkali metal hydrides, such as sodium hydride, alkali metal carbonates, such as sodium carbonate, or alkali metal alkoxides such as sodium or-potassium methoxide, ethoxide or t-butoxide. The alkylation reaction is conveniently carried out at a temperature of from 25 to 100° C.

Alternatively, a compound of formula (I) wherein one or more of $R^1$ and $R^2$ represents a hydrogen atom may be converted to another compound of formula (I) by reductive alkylation as described by Borch in J.Org.Chem. 37 (10), 1673 (1972). Reductive alkylation with an appropriate aldehyde or ketone may be effected using an alkaline earth metal borohydride or cyanoborohydride. The reaction may be effected in an aqueous or non-aqueous reaction medium, conveniently in an alcohol, e.g. methanol or ethanol or an ether, e.g. dioxan or tetrahydrofuran, optionally in the presence of water. The reaction may conveniently be carried out at a temperature in the range of 0 to 100° C., preferably 5 to 50° C. Conveniently the reaction may be effected with sodium cyanoborohydride under acidic conditions e.g. in the presence of acetic acid. Alternatively, the alkylation may be performed by heating a compound of formula (I) wherein one or more of $R^1$ and $R^2$ represents a hydrogen atom with the appropriate aldehyde or ketone such as formaldehyde in the presence of an acid such as formic acid at a temperature of 0 to 150°, preferably at about 90° C.

Compounds of formula (I) wherein X is an aryl substituted by a —$NHCO(CH_2)_mNR^1R^2$ group may be prepared by reacting a compound of formula (I) wherein X is an aryl substituted by an amino group with an appropriate acid under conditions selected to form an amide bond. Various amide bond forming procedures may be employed including dicyclohexylcarbodiimide, 2-chloro-1-methylpyridinium iodide, and benzotriazol-1-yloxytris (dimethylamino) phosphonium hexafluorophosphate.

According to another general process (E), a compound of formula (I) according to the invention, or a salt thereof may be prepared by subjecting a protected derivative of a compound of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1981).

Conventional amino protecting groups may include for example aralkyl groups, such as benzyl, diphenylmethyl or triphenylmethyl groups; and acyl groups such as N-benzyloxycarbonyl or t-butoxycarbonyl. Thus, compounds of general formula (I) wherein one or more of the groups $R^1$ and $R^2$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl, silicon protecting groups, such as trimethylsilyl or t-butyl dimethylsilyl groups, or as tetrahydropyran derivatives.

Removal of any protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation; silicon protecting groups may be removed, for example, by treatment with fluoride ion or by hydrolysis under acidic conditions; tetrahydropyran groups may be cleaved by hydrolysis under acidic conditions.

As will be appreciated, in any of the general processes (A) to (D) described above it may be desirable or even necessary to protect any sensitive groups in the molecule as just described. Thus, a reaction step involving deprotection of a protected derivative of general formula (I) or a salt thereof may be carried out subsequent to any of the above described processes (A) to (D).

Thus, according to a further aspect of the invention, the following reactions may, if necessary and/or desired be carried out in any appropriate sequence subsequent to any of the processes (A) to (D):

(i) removal of any protecting groups; and
(ii) conversion of a compound of formula (I) or a salt thereof into a pharmaceutically acceptable salt or solvate thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

Typically, biological activity of the compounds of formula (I) resides in the S enantiomer, and the R enantiomer has little or no activity. Thus, the S enantiomer of a compound of formula (I) is generally preferred over a mixture of R and S such as the racemic mixture. However, if the R enantiomer were desired, e.g., for control studies or synthesis of other compounds, it could be conveniently prepared by the procedure above using the R enantiomer of the compound of formula (VII) prepared according to the teachings of '512.

A compound of formula (I) may be purified by conventional methods of the art, e.g., chromatography, distillation or crystallization.

Cleavable Complex in vitro Assay

The relative topoisomerase Type I inhibitory activity of the compounds of formula (I) was determined by cleavable complex in vitro assay. This assay performed according to the method described in Hsiang, Y. et al., *J. Biol. Chem.*, 260:14873–14878 (1985), correlates well with in vivo antitumor activity of topoisomerase inhibitors in animal models of cancer, e.g., camptothecin and its analogs. See Hsiang et al., *Cancer Research,* 49:4385–4389 (1989) and Jaxel et al., *Cancer Research,* 49:1465–1469 (1989).

The compound of Example 15 exhibited observable topoisomerase Type I inhibitory activity (IC50) at concentrations greater than 2000 nM (weakly to moderately active), the compound of Example 31 at concentrations greater than 1000 nM, the compounds of Examples 17, 18, 28 and 36 at concentrations greater than 500 nM and all the remaining exemplified compounds at concentrations of less than 500 nM (very active). The term "IC50" means the concentration of a compound of formula (I) at which 50% of the DNA substrate has been captured by topoisomerase 1.

The compounds of formula (I) are active against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung (including non-small cell), bone, connective tissue, skin, colon, breast, cervix uteri, corpus endometrium, ovary, prostate, testis, bladder, kidney and other urinary tissues, eye, brain and central nervous system, thyroid and other endocrine glands, leukemias (lymphocytic, granulocytic, monocytic), Hodgkin's disease, non-Hodgkin's lymphomas, multiple myeloma, etc. Herein the terms "tumor", "cancer" and "cancerous growths" are used synonymously.

The amount of compound of formula (I) required to be effective as an antitumor agent will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective antitumor dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 75 to about 7500 mg per day, and a typical dose would be about 800 mg per day. If discrete multiple doses are indicated, treatment might typically be 200 mg of a compound of formula (I) given 4 times per day.

Formulations

Formulations of the present invention, for medical use, comprise an active compound, i.e., a compound of formula (I), together with an acceptable carrier therefor and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal or vaginal administration may be presented as a suppository with a conventional carrier, e.g., cocoa butter or Witepsol S55 (trademark of Dynamite Nobel Chemical, Germany, for a suppository base).

For transdermal administration the compounds according to the invention may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride. Useful formulations also comprise concentrated solutions or solids containing the compound of formula (I) which upon dilution with an appropriate solvent give a solution suitable for parenteral administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*. As used here in the term "room temperature" means about 25° C.

Example 1

7-Methylthiomethyl-10,11-(ethylenedioxy)-20(S)-camptothecin (A) 1-Methylthio-2[2'amino-4'5-(ethylenedioxy)]acetophenone A mixture of 1 chloro-[2'-amino-4'5'ethylenedioxy]acetophenone (I) (0.25 g, 1.1 mmol) and sodium thiomethoxide (0.1 g, 1.4 mmol) in dry tetrahydrofuran (5 mL) is heated at reflux for about 16 h. The mixture is cooled to room temperature and the solvent is evaporated. The residue is treated with diethyl ether (25 mL) and filtered. The filtrate is evaporated to give the title compound as a yellow solid 0.2589 (98%). Mp. 103–105° C. MS. calcd. for $C_{11}H_{14}O_3NS$, 240.0694. Found 240.0691.

(B) 5'(R,S)-1,5-Dioxo-(5'-ethyl-5'-hydroxy-2'H,5'H-6-oxopyrano)[3',4'-f]$\Delta^6$, $^8$-tetrahydroindolizine and 5'(S)-1,5-Dioxo-(5'-ethyl-5'-hydroxy-2'H,5'H,6'H-6-oxopyrano)[3',4'-f]$\Delta^6$, $^8$-tetrahydroindolizine (tricyclic ketones of formula (VII))

The compounds, referred to herein as "tricyclic ketone (R,S)" and "tricyclic ketone (S)" respectively or collectively as "a compound of formula (VII)", are prepared according to the procedure taught by Wani et al., in '512. Note that the corresponding R enantiomer may also be prepared by the procedure of '512.

(C) 7-Methylthiomethyl-10,11-(ethylenedioxy)-20(S)-camptothecin

A mixture of 1-methylthio-[2'amino-4'5'-(ethylenedioxy)]acetophenone (0.05 g, 0.22 mmol), tricyclic ketone(S)(0.05 g, 0.19 mmol) and acetic acid (0.02 mL, 0.38 mmol) in dry toluene (2 mL) is placed in an oil bath at 130° C. After about 2 min. a catalytic amount of p-toluenesulfonic acid is added and the mixture is heated at reflux for about 16 h. The mixture is cooled to room temperature and filtered to give the title compound as a tan solid, 0.0669, (76%). Mp. 232–234° C. MS calcd. for $C_{24}H_{23}O_6N_2S$, 467.1277. Found, 467.1267.

Example 2

7-Methylthiomethyl-10,11-(methylenedioxy)-20(S)-camptothecin (A) 1-Methylthio-[2'amino-4'5'(methylenedioxy)]acetophenone The same procedure as Example 1, part (A) is used except an equivalent amount of 1-chloro[2'-amino-4'5'methylenedioxy]acetophenone (0.46 g, 2 mmol) is used in place of 1-chloro-[2'-amino-4'5'-ethylenedioxyacetophenone. The title compound 0.326 g, (72%), is obtained.

(B) 7-Methylthiomethyl-10,11-(methylenedioxy)-20(S)-camptothecin

The same procedure as Example 1, part (C) is used except that an equivalent amount of 1-methylthio-[2'-amino-4'5'-methylenedioxy)]-acetophenone is reacted with the S-tricyclic ketone (0.11 g, 0.42 mmol). The title compound is obtained 0.139 g (73%). Mp 246–248° C. MS calcd. for $C_{23}H_{21}N_2O_6S$, 453.1120. Found 453.1119.

Example 3
7-(2-Pyridylthio)methyl-10,11-(ethylenedioxy)-20(S) camptothecin (A) 1-(2-Pyridylthio)-[2'-amino-4'5'-(ethylenedioxy)] acetophenone A slurry of sodium hydride (0.012 g, 0.5 mmol) in dry THF (1 mL) under nitrogen is cooled to 0° C. in an ice bath. A solution of 2-pyridinethiol (0.054 g, 0.48 mmol) in dry THF (1 mL) is added and the mixture is stirred for 10 min. A solution of 1-chloro-[2'-amino-4'5'-ethylenedioxy]acetophenone (0.1 g, 0.44 mmol) in dry THF (2 mL) is added and the mixture is stirred at room temperature for 1 h. The solvents are evaporated and the residue is purified by chromatography on silica gel to give the title compound 0.108 g (81%). Mp. 106–107° C. MS calcd. for $C_{15}H_{15}N_2O_3S$ 303.0803. Found, 303.0795.

(B) 7-(2-Pyridylthio)methyl-10,11-(ethylenedioxy)-20(S)-camptothecin

The same procedure as Example 1, part C is used except that an equivalent amount of the compound of part (A) in this example is reacted with the tricyclic ketone (S) (0.025 g, 0.09 mmol) to obtain the title compound 0.04 g, (79%). Mp. 240–245° C. MS calcd. for $C_{28}H_{24}N_3O_6S$, 530.1386. Found, 530.1392.

Example 4
7-(2-Pyridylthio)methyl-10,11-(methylenedioxy)-20(S)-camptothecin (A) 1-(2-Pyridylthio)-[2'-amino-4'5'-(methylenedioxy)] acetophenone The same procedure as Example 3, part A is used except 0.2 g, 0.93 mmol 1-chloro-[2'-amino-4'5'-methylenedioxy]acetophenone is used in place of 1-chloro-[2'-amino-4'5'-ethylene-dioxy]acetophenone to obtain the title compound, 0.2399 (88%). Mp. 103–105° C. MS MH+303.

(B) 7-(2-Pyridylthio)methyl-10,11-(methylenedioxy)-20(S)-camptothecin

In a manner similar to Example 1, part (C), the compound of Example 4, part (A) is reacted with the S-tricyclic ketone (0.05 g, 0.19 mmol) to obtain the title compound 0.073 g (74%). Mp. 245–248° C. MS calcd. for $C_{27}H_{22}N_3O_6S$, 516.1228. Found, 516.1209.

Example 5
7-(2-Pyrimidylthio)methyl-10,11-(methylenedioxy)-20(S)-camptothecin (A) 1-(2-Pyrimidinylthio)-[2'-amino-4'5'-(methylenedioxy)]acetophenone In a similar manner to Example 3, part (A), in place of 2-pyridylthiol, 2-pyrimidinylthiol is reacted with 1-chloro-[2'-amino-4'5'-methylenedioxy]acetophenone (0.29, 0.93 mmol) to obtain the title compound, 0.234 g (88%). Mp. 162–164° C. MS calcd. for $C_{13}H_{12}N_3O_3S$ 290.0598. Found, 290.0611.

(B) 7-(2-Pyrimidylthio)methyl-10,11-(methylenedioxy)-20(S)-camptothecin

In a manner similar to Example 1, part (C), the compound of Example 5, part (A) is reacted with the tricyclic ketone (S) (0.059, 0.19 mmol) to obtain the title compound 0.013 g (13%). Mp. 245–248° C. MS calcd. for $C_{26}H_{20}N_4O_6S$, 517.1180. Found, 517.1179.

Example 6
7-(4-Nitrophenylthio)methyl-10,11-(methylenedioxy)-20(S)-camptothecin (A) 1-(4-Nitrophenylthio)-[2'-amino-4'5'-(methylenedioxy)]acetophenone In a similar manner to Example 3, part (A), in place of 2-pyridylthiol, an equivalent amount of 4-nitrophenylthiol is used and reacted with 1-chloro-[2'-amino-4'5'-methylenedioxy]acetophenone (0.2 g, 0.93 mmol) to obtain the title compound, 0.245 g (78%).

(B) 7-(4-Nitrophenylthio)methyl-10,11-(methylenedioxy)-20(S)-camptothecin

In a manner similar to Example 1, part (C), the compound of part (A) of this example is reacted with the S-tricyclic ketone (0.03 g, 0.11 mmol) to obtain the title compound, 0.035 g (55%). Mp. 205° C. decomp. MS MII+560.

Example 7
7-(4-Acetamidophenylthio)methyl-10,11-(methylenedioxy)-20(S)-camptothecin (A) 1-(4-Acetamidophenylthio)-[2'-amino-4'5'-(methylenedioxy)]acetophenone In a similar manner to Example 3, part (A), in place of 2-pyridylthiol, an equivalent amount of 4-acetamidophenylthiol is reacted with 1-chloro-[2'-amino-4'5'-methylenedioxy]acetophenone (0.2 g, 0.93 mmol) to obtain the title compound, 0.272 g (90%). Mp. 168–170° C. MS MH+345.

(B) 7-(4-Acetamidophenylthio)methyl-10,11-(methylenedioxy)-20(S)-camptothecin

In a similar manner to Example 1, part (C), the compound of part (A) of this example is reacted with the S-tricyclic ketone (0.05 g, 0.19 mmol) to obtain the title compound, 0.0789 (72%). Mp. 205–207° C. MS calcd. for $C_{30}H_{22}N_3O_7S$, 5572.1490. Found, 572.1502.

Example 8
7-Methylsulfinylmethyl-10,11-(ethylenedioxy)-20(S)-camptothecin

A solution of 7-methylthiomethyl-10,11-(ethylenedioxy)-20(S)-camptothecin (0.03 g, 0.064 mmol) in chloroform:methanol (10:1, 5 mL) is cooled to −78° C. in an acetone dry ice bath. In a separate flask, a saturated solution of ozone in dichloromethane is prepared and added to the solution until no starting material remains as evidence by TLC. The solvents are evaporated and the residue is purified by chromatography to give the title compound as a yellow solid, 0.023 g (74%). Mp. 240–244° C. MS calcd. for $C_{24}H_{23}N_2O_7S$, 483.1226. Found, 483.1213.

Example 8A
7-Methylsulfinylmethyl-10,11-(ethylenedioxy)-20(S)-camptothecin

Hydrogen peroxide, 30% aqueous solution, (0.06 mL, 0.59 mmol) is added to a solution of 7-methylthiomethyl-10,11-(ethylenedioxy)-20(S)-camptothecin (0.25 g, 0.53 mmol) in acetic acid (5 mL) at room temperature and the mixture is stirred for about 16 h. The solvent is evaporated and the residue is purified by chromatography to give the title compound, 0.1749 (67%).

Example 9
7-Methylsulfinylmethyl-10,11-(methylenedioxy)-20(S)-camptothecin

In a similar manner to Example 8 using 7-methylthiomethyl-10,11-(methylenedioxy)-20(S)-camptothecin (0.05 g, 0.11 mmol) obtained as in Example 1 in place of 7-methylthiomethyl-10,11-(ethylenedioxy)-20(S)-camptothecin, the title compound is obtained 0.037 g (71%). Mp. 236–240° C. MS MH+469.

Example 10
7-(2-Pyridylsulfinyl)methyl-10,11-(methylenedioxy)-20(S)-camptothecin In a similar manner to Example 8A using 7-(2-pyridinythio)methyl-10,11-(methylenedioxy)-20(S)- camptothecin (0.029, 0.04 mmol) obtained as in Example 4 in place of 7-methylthiomethyl-10,11-(ethylenedioxy)-20 (S)-camptothecin the title compound is obtained 0.016 g (77%). Mp. 220–225° C. MS calcd. for $C_{27}H_{22}N_3O_7S$, 532.1177. Found, 532.1172.

Example 11

7-Methylsulfonylmethyl-10,11-(ethylenedioxy)-20(S)-camptothecin

Hydrogen peroxide (0.021 mL, 0.21 mmol) is added to a solution of 7-methylthiomethyl-10,11-(ethylenedioxy)-20 (S)-camptothecin (0.039, 0.06 mmol) obtained as in Example 1 in acetic acid (1.0 mL) and the mixture is warmed to about 75° C. for about 5 h. The mixture is cooled to room temperature and the solvent is evaporated. The residue is treated with hot ethanol (2 mL), cooled to room temperature and filtered to give the title compound, 0.020 g (65%). Mp. 247–250° C. MS calcd. for $C_{24}H_{23}O_8N_2S$, 499.1175. Found, 499.1186.

Example 12

7-Methylsulfonylmethyl-10,11-(methylenedioxy)-20(S)-camptothecin

In a similar manner to Example 11 using 7-methylthiomethyl-10,11-(methylenedioxy)-20(S)-camptothecin (0.039, 0.07 mmol). obtained as in Example 2 in place of 7-methylthiomethyl-10,11-(ethylenedioxy)-20(S)-camptothecin, the title compound is obtained. 0.024 g (77%). Mp. 262–265° C. Nominal Mass Spectrum M+1 485.

Example 13

7-Dimethylphosphonomethylene-10,11-methylenedioxy-20 (S)-camptothecin (A) 3,4-Methylenedioxyacetanilide To commercially available 3,4-methylenedioxy aniline (17.0 g, 124 mmol) and sodium carbonate (15.5 g, 136 mmol) in chloroform (90 mL) at 5° C. is added acetyl chloride (8.8 g, 124 mmol) dropwise with stirring. The reaction is allowed to warm to room temperature and stirring is continued for about 18 hours. The reaction mixture is washed twice with about 50 mL of 1 N HCl and the organic layer is dried (MgSO4) and the solvent removed to yield a brown solid. Recrystallization from water with activated carbon treatment yields 3,4-methylenedioxyacetanilide (9.34 g, 42.1% of theory) as a light brown solid.

| Elemental analysis: ($C_9H_9NO_3$) | | |
| --- | --- | --- |
| % C | % H | % N |
| Found: 60.34 | 5.04 | 7.79 |
| Calculated 60.33 | 5.06 | 7.82 |

(B) 2-Acetylamino-4',5'-methylenedioxy-2-chloroacetophenone

To a mixture of zinc chloride (24.3 g, 178.3 mmol) and chloroacetyl-chloride (16.1 mL, 202.1 mmol) in nitromethane (85 mL), under nitrogen, at room temperature, with stirring, is added, dropwise, 3,4-methylenedioxyacetanilide (8.96 g, 50.0 mmol) in nitromethane (15 mL). This mixture is then heated at reflux for 1.5 hrs, allowed to cool to room temperature, poured over ice, extracted with methylene chloride, which is then removed by evaporation, to yield a brown solid. This solid is recrystallized from an ethyl acetate/hexane mixture (including treatment with activated charcoal) to yield 2'-acetylamino-4',5'-methyl-enedioxy-2-chloroacetophenone (831.3 mg, 6.5% of theory) as yellow crystals.

1H-NMR (CDCl3): δ 8.45 (s, 1H); 7.2 (s, 1H); 6.09 (s, 2H); 4.65 (s, 2H); 2.25 (s, 3H).

(C) 3,4-Methylenedioxypivaloylanilide

This compound is prepared by the method of Example 13(A) except an equivalent amount of 2,2-dimethylpropanoyl chloride is used in place of acetyl chloride.

(D) 2'-Pivoylamino-4',5'-methylenedioxy-2-chloroacetophenone

This compound is prepared by the method of Example 13(B) except an equivalent amount of 3,4-methylenedioxypivaloylanilide is used in place of 3,4-methylenedioxyacetanilide.

(E) 2'-Amino-4',5'-methylenedioxy-2-chloroacetophenone

To 2'-acetylamino-4',5'-methylenedioxy-2-chloroacetophenone (0.9 g, 3.53 mmol) or an equivalent amount of 2'-pivoylamino-4',5'-methylenedioxy-2-chloroacetophenone in ethanol (60 mL) at about 5° C. is added, dropwise, conc. HCl (12.5 mL, 149.7 mmol). The reaction mixture is then heated at reflux for about an hour, then poured over 2 N NaOH/ice (80 mL/60 g) and washed with ethyl acetate (3×70 mL). The organic portions are combined and washed with brine (50 mL), dried (anhydrous sodium sulfate) and concentrated in vacuo to yield a greenish-yellow solid. This solid is recrystallized from ethyl acetate/isopropanol/hexane, treated with activated charcoal, to yield 2'-amino-4',5'-methylenedioxy-2-chloroacetophenone (0.39 g, 52% of theory).

| Elemental analysis: ($C_9H_8NO_3Cl$) | | |
| --- | --- | --- |
| % C | % H | % N |
| Found: 50.66 | 3.80 | 6.47 |
| Calculated 50.60 | 3.77 | 6.56 |

(F) 7-Chloromethyl-10,11-methylenedioxy-20(S)-camptothecin

Following the general procedure for camptothecin taught in '512, 2'-amino-4',5'-methylenedioxy-2-chloroacetophenone is stirred in refluxing toluene (50 mL) with tricyclic ketone (S) (256.3 mg, 0.97 mmol) under a Dean-Stark trap for half an hour. The reaction is then cooled and the solid filtered and washed with toluene and ethanol to yield 7-chloromethyl-10,11-methylenedioxy-20(S)-camptothecin, (G) 7-Dimethylphosphonemethylene-10,11-methylenedioxy-20(S)-camptothecin chloride A dry 25 mL flask is fitted with a magnetic stir bar and purged with dry nitrogen. The flask is then charged with 7-chloromethylene-10,11-(methylenedioxy)-20(S)-camptothecin (100 mg, 0.23 mmol), dry DMF (3 mL) and trimethylphosphite (3 mL, 25 mmol). A reflux condenser is fitted and the mixture is heated at 110° C. When the reaction is complete, (thin layer chromatography: 5% methanol:ethyl acetate), the reaction is cooled and the volatiles are removed under vacuum. The reaction mixture is purified directly by reverse phase HPLC to give the title compound, 66 mg (58%). MS calcd. for $C_{24}H_{23}O_9N_2P$, 515.1219. Found 515.1207

Example 14

7-Dimethylphosphonomethylene-10,11-(ethylenedioxy)-20 (S)-camptothecin chloride (A) 7-Chloromethyl-10,11-(ethylenedioxy)-20(S)-camptothecin This compound is prepared by the procedure of Example 13, except in parts (A) and (C) an equivalent amount of 3,4-ethylenedioxy aniline is used in place of 3,4-methylenedioxy aniline.

(B) 7-Dimethylphosphonomethylene-10,11-(ethylenedioxy)-20(S)-camptothecin

7-Chloromethylene-10,11-(ethylenedioxy)-20(S)-camptothecin (0.1 g, 0.23 mmol) is reacted with trimethylphosphite as in Example 13, part (G) to obtain the title compound, 0.076 g (65%). MS calcd. for $C_{225}H_{225}O_9N_2P$, 529.1376. Found, 529.1351.

Example 15

7-Di-n-butylphosphonomethylene-10,11-(ethylenedioxy)-20(S)-camptothecin

7-Chloromethylene-10,11-(ethylenedioxy)-20(S)-camptothecin (0.1 g, 0.23 mmol) obtained as in Example 14, part (A) is reacted with tri-n-butylphosphite as in Example 13, part (G) to obtain the title compound, 0.0489 (35%). Mp. >200° C. (d). Nominal Mass Spectrum M+1 612. Exact MS calcd. 612.2237. Found 612.2233.

Example 16

7-(4-Aminophenylthio)methyl-10,11-(methylenedioxy)-20(S)-camptothecin

A mixture of 7-(4-acetamidophenylthio)methyl-10,11-(methylenedioxy)-20(S)-camptothecin (0.025 g, 0.04 mmol) and 2 N aqueous HCl (1 mL) is heated at reflux for about 2 h. The mix is filtered while hot and the filtrate is lyophilized to give the title compound as a hydrochloride salt, 0.013 g (58%). Mp. >300° C. MS calcd. for $C_{28}H_{24}N_3O_6S$, 530.1386. Found, 530.1390.

Example 17

7-(4-Acetamidophenylthio)methyl-10,11-(ethylenedioxy)-20(S)-camptothecin (A) 1-(4-Acetamidophenylthio)-[2'-amino-4'5'-(ethylenedioxy)]acetophenone The same procedure as Example 3, part A is used except 0.3 g, 1.32 mmol 1-chloro-[2'-amino-4'5'-ethylenedioxy]acetophenone is used in place of 1-chloro-[2'-amino-4'5'-methylenedioxy]acetophenone to obtain the title compound, 0.305 g (64%).

(B) 7-(4-Acetamidophenylthio)methyl-10,11-(ethylenedioxy)-20(S)-camptothecin

In a similar manner to Example 1, part (C), the compound of Example 17, part (A) is reacted with the S-tricyclic ketone (0.1 g, 0.38 mmol) to obtain the title compound, 0.154 g (69%). Mp. 212–216° C. MS calcd. for $C_{29}H_{26}N_3O_6S$, 544.1542. Found, 544.1545.

Example 18

7-(4-Aminophenylthio)methyl-10,11-(ethylenedioxy)-20(S)-camptothecin

In a manner similar to Example 16, except 7-(4-acetamidophenylthio)methyl-10,11-(ethylenedioxy)-20(S)-camp-tothecin (0.1 2 g, 0.20 mmol) is used in place of 7-(4-acetamidophenylthio)methyl-10,11-(methylenedioxy)-20(S)-camptothecin to give the title compound as a hydrochloride salt, 0.0829 (69%). Mp. >300° C. MS calcd. for $C_{29}H_{26}N_3O_6S$. 544.1542. Found. 544.1545.

Example 19

7-(2-Aminoethylthio)methyl-10,11-(ethylenedioxy)-20(S)-camptothecin (A) 1-[(N-Benzyloxycarbonyl) 2-aminoethylthio]-[2'-amino-4'5'-(ethylenedioxy)]acetophenone The same procedure as Example 3, part A is used except 0.4 g, 1.86 mmol 1-chloro-[2'-amino-4'5'-ethylenedioxy] acetophenone is used in place of 1-chloro-[2'-amino-4'5'-methylenedioxy]acetophenone to obtain the title compound, 0.423 g (60%).

(B) 7-[(N-Benzyloxycarbonyl)2-aminoethylthio]methyl-10,11-(ethylenedioxy)-20(S)-camptothecin In a similar manner to Example 1, part (C), the compound of Example 19, part (A) is reacted with the S-tricyclic ketone (0.22 g, 0.84 mmol) to obtain the title compound, 0.37 g (70%). Mp. 210–213° C. MS MH+629.9.

(C) 7-(2-Aminoethylthio)methyl-10,11-(ethylenedioxy)-20(S) camptothecin

A mixture of 7-[(N-benzyloxycarbonyl)2-aminoethylthio] methyl-10,11-(ethylenedioxy)-20(S)-camptothecin (0.33 g, 0.52 mmol) and 50% aqueous trifluoroacetic acid (25 mL) is heated at reflux for about 18 h. The mix is cooled to room temperature and filtered. The filtrate is evaporated and the residue is washed with ethyl acetate and acetone and dried under vacuum to give the title compound as a trifluoroacetate salt, 0.28 g (88%). Mp. >300° C. MS calcd. for $C_{25}H_{26}N_3O_6S$, 496.1542. Found, 496.1555.

Example 20

7-(2-Dimethylaminoethylthio)methyl-10,11-(ethylenedioxy)-20(S)-camptothecin

A mixture of 7-(2-aminoethylthio)methyl-10,11-(ethylenedioxy)-20(S)-camptothecin, trifluoroacetate salt (0.419, 0.23 mmoll) and 37% aqueous formaldehyde (0.1 mL) in acetonitrile (5 mL) and acetic acid (1 mL) is cooled to 0C. Sodium cyanoborohydride (9.022 g, 0.35 mmol) is added in portions over 2 minutes and the mix is stirred at 0° C. for 30 minutes. The solvent is evaporated under reduced pressure and the residue is purified by reverse phase high pressure chromatography on a C-8 column using 2% aqueous trifluoroacetic acid: acetonitrile (4:1) as eluent to give the title compound as a trifluoroacetate salt, 0.065 g (44%). Mp. 300° C. MS calcd. for $C_{27}H_{30}N_3O_6S$, 524.1855. Found, 524.1863.

Example 21

7-(3-Aminopropylthio)methyl-10,11-(ethylenedioxy)-20(S)-camptothecin (A)1-[(N-Benzyloxycarbonyl)-3-aminopropylthio]-[2'-amino-4',5-(ethylenedioxy)]acetophenone The same procedure as Example 3, part A is used to obtain the title compound, 5.7 g (68%).

(B) 7-[(N-Benzyloxycarbonyl)-3-aminopropylthio] methyl-10,11-(ethylenedioxy)-20(S)-camptothecin In a similar manner to Example 1, part (C), the compound of Example 21, part (A) is reacted with the S-tricyclic ketone (0.409, 1.52 mmol) to obtain the title compound, 0.58 g (59%).

(C) 7-(3-Aminopropylthio)methyl-10,11-(ethylenedioxy)-20(S)-camptothecin

A mixture of the compound of Example 21, part (B) and 30% hydrogen bromide in acetic acid is reacted at room temperature for about 1 h. The solvent is evaporated and the residue is purified by reverse phase high pressure liquid chromatography on a C-8 column using 2% trifluoroacetic acid:acetonitrile (4:1) as eluent to give the title compound as a trifluoroacetate salt, 0.246 g (90%). Mp. >300° C. MS MH+510.

Example 22

7-(3-Dimethylaminopropylthio)methyl-10,11-(ethylenedioxy)-20(S)-camptothecin

In a similar manner to Example 20, the compound of Example 21, part (C) is reacted with aqueous formaldehyde and sodium cyanoborohydride to give the title compound as a trifluoroacetate salt, 0.02 g (65%). Mp. 150° C. (dec). MS MH+538.

Example 23
7-(2-Methylaminoethylthio)methyl-10,11-(ethylenedioxy)-20(S)-camptothecin (A) 1-[(N-Benzyloxycarbonyl)-2-methylaminoethylthio]-[2'-amino-4,5'-(ethylenedioxy)]acetophenone The same procedure as Example 3, part A is used to obtain the title compound, 0.26 g (71%).

(B) 7-[(N-Benzyloxycarbonyl)-2-methylaminoethylthio] methyl-10,11-(ethylenedioxy)-20(S)-camptothecin In a similar manner to Example 1, part (C), the compound of Example 21, part (A) is reacted with the S-tricyclic ketone (0.059, 0.19 mmol) to obtain the title compound, 0.068 g (55%).

(C) 7-(2-Methylaminoethylthio)methyl-10,11-(ethylenedioxy)-20(S)-camptothecin

A mixture of the compound of Example 23, part (B) and 30% hydrogen bromide in acetic acid is reacted as described in Example 21, part (C) to give the title compound as a trifluoroacetate salt, 0.013 g (67%). Mp.>300° C. MS MH+510.

Example 24
7-(2-Aminoethylthio)methyl-10,11-(methylenedioxy)-20(S)-camptothecin (A)1-[(N-Benzyloxycarbonyl)-2-aminoethylthio]-[2'-amino-4',5'-(methylenedioxy)]-acetophenone The same procedure as Example 3, part A is used except 0.384 g, 1.8 mmol 1-chloro-[2'-amino-4',5'-methylenedioxy] acetophenone is used in place of 1-chloro-[2'-amino-4',5'-ethylenedioxy]acetophenone to obtain the title compound, 0.488 g (70%).

(B) 7-[(N-Benzyloxycarbonyl)-2-aminoethylthio]methyl-10,11-(methylenedioxy)-20(S)-camptothecin In a similar manner to Example 1, part (C), the compound of Example 24, part (A) is reacted with the S-tricyclic ketone (0.03 g, 0.11 mmol) to obtain the title compound, 0.059 g (87%). Mp. 210° C. (dec). MS MH+616.

(C) 7-(2-Aminoethylthio)methyl-10,11-(methylenedioxy)-20(S)-camptothecin

A mixture of the compound of Example 24, part (B) and 30% hydrogen bromide in acetic acid is reacted as described in Example 21, part (C) to give the title compound as a trifluoroacetate salt, 0.0055 g (58%). Mp. >300° C. MS MH+482.

Example 25
7-(2-Methylaminoethylsulfinyl)methyl-10,11-(ethylenedioxy)-20(S)-camptothecin A mixture of 7-(2-methylaminoethylthio)methyl-10,11-(ethylenedioxy)-20(S)-camptothecin (0.009 g, 0.01 mmol) and sodium periodate (0.00359, 0.02 mmol) in water is reacted at room temperature for about 1 h. The solvent is evaporated and the residue is purified by high pressure liquid chromatography on a C-8 column using 2% trifluoroacetic acid:acetonitrile (4:1) as eluent to give the title compound as a trifluoroacetate salt, 0.003 g (33%). Mp. >300° C. MS MH+526.

Example 26
7-(3-Aminopropylsulfinyl)methyl-10,11-(ethylenedioxy)-20(S)-camptothecin The compound of Example 21 was reacted in a similar manner as described in Example 25 to give the title compound as a trifluoroacetate salt, 0.0063 g (60%). MS MH+526. Mp. 140° C. (d).

Example 27
7-(3-Dimethylaminopropylsulfinyl)methyl-10,11-(ethylenedioxy)-20(S)-camptothecin The compound of Example 22 is found to readily oxidize during purification to give the title compound as a trifluoroacetate salt. Mp. 195° C. (dec). MS MH+554.

Example 28
7-(4-(2-Dimethylaminoacetamido)phenylthio)methyl-10,11-(ethylenedioxy)-20(S)-camptothecin A mixture of 7-(4-aminophenylthio)methyl-10,11-(ethylenedioxy)-20(S)-camptothecin (0.0045 g, 0.008 mmol), NN-dimethylglycine hydrochloride (0.0026 g, 0.018 mmol) and dicyclohexylcarbodiimide (0.00429, 0.02 mmol) in pyridine (1 mL) is reacted at room temperature for about 3 h. The solvents are evaporated and the residue is purified by reverse phase high pressure liquid chromatography on a C-8 column using 2% trifluoroacetic acid:acetonitrile (4:1) as eluent to give the title compound as a trifluoroacetate salt, 0.0023 g (40%). Mp. >300° C. MS MH+629.

Example 29
7-Pyridinium methylene-10,11-methylenedioxy-20(S)-camptothecin Chloride (Compound 29)

A) 7-Pyridinium methylene-10,11-methylenedioxy-20(S)-camptothecin chloride

7-Chloromethyl-10,11-methylenedioxy-(S)-camptothecin (0.119, 0.25 mmol), prepared according to Example 13(A)–(F) is added to anhydrous pyridine (2 ml) under a blanket of nitrogen at room temperature. The reaction mixture was stirred for about 4 hrs and then 1.0 ml of diethyl ether was added to precipitate the desired product. A yellow solid was collected by filtration, washed once with ethanol (absolute, 2 mls) and twice with diethyl ether. The compound was dried under vacuum to yield 7-pyridiniummethylene-10,11-methylenedioxy-20(S)-camptothecin chloride (116 mg, 84%). Nominal Mass Spectrum M+:484. m.p. >285° C.

| Elemental analysis: ($C_{27}H_{22}N_3O_6Cl2H_2O$) | | | |
|---|---|---|---|
| | % C | % H | % N |
| Calculated: | 58.52 | 4.68 | 7.56 |
| Found | 58.74 | 4.63 | 7.53 |

(B) Open E ring form

The compound of part (A) can be treated with an equivalent amount of sodium hydroxide to form the corresponding open E ring form. Treatment of the latter with an equivalent amount of hydrochloric acid closes the E ring and thereby reforms the compound of part (A).

Example 30
7-Pyridinium methylene-10,11-ethylenedioxy-20(S)-camptothecin chloride (Compound 30)

This compound is prepared by the procedure of Example 29, part (A), except that an equivalent amount of 7-chloromethyl-10,11-ethylenedioxy-20(S)-camptothecin prepared according to Example 14(A) was used in place of 7-chloromethyl-10,11-methylenedioxy-20(S)-camptothecin. Nominal Mass Spectrum M+: 498 mp >300° C.

Example 31
7-Pyridinium methylene-10,11 ethylenedioxy-20(R,S)-camptothecin chloride (Compound 31)

(A) 7-Chloromethyl-10,11-ethylenedioxy-20(R,S)-camptothecin

This compound is prepared by the procedure of Example 13 except in parts (A) and (C) an equivalent amount of 3,4-ethylenedioxy aniline is used in place of 3,4-methylenedioxy aniline and in part (G) an equivalent amount of tricyclic ketone (R,S) is used in place of tricyclic ketone (S).

(B) 7-Pyridinium methylene-10,11-ethylenedioxy-20(R,S)-camptothecin

This compound is prepared by the procedure of Example 29, part (A), except that an equivalent amount of 7-chloromethyl-10,11-ethylenedioxy-20(R,S)-camptothecin was used in place of 7-chloromethyl-10,11-methylenedioxy-20(S)-camptothecin. Nominal Mass Spectrum M+: 498 mp: >290° C.

Example 32

7-(3'-Methylimidazolium) methylene-10,11-ethylenedioxy-20(S)-camptothecin chloride (Compound 32)

The same procedure as Example 29, part (A), is used except that an equivalent amount of 3-methylimidazole is used in place of pyridine and an equivalent amount of 7-chloromethyl-10,11-ethylenedioxy-20(S)-camptothecin, prepared according to Example 14(A) is used in place of 7-chloromethyl-10,11-methylenedioxy-20(S)-camptothecin. Nominal Mass Spectrum M+: 501 mp: >303° C.

Example 33

7-(3'-Methylimidazolium) methylene-10,11-methylenedioxy-20(S)-camptothecin chloride (Compound 33)

The same procedure as Example 29, part (A), is used except that an equivalent amount of 3-methylimidazole is used in place of pyridine. Nominal Mass Spectrum M+: 487 mp: 242° C. (d)

Elemental Analysis $C_{26}H_{23}N_4O_6Cl.H_2O$

| | Calc. | Found |
|---|---|---|
| C | 57.71 | 57.67 |
| H | 4.62 | 4.48 |
| N | 10.36 | 10.20 |

Example 34

7-Pyridazinium methylene-10,11-methylenedioxy-20(S)-camptothecin chloride (Compound 34)

The same procedure as Example 29, part (A), is used except that an equivalent amount of pyridazine is used in place of pyridine. Nominal Mass Spectrum M+: 485 mp: >275° C.

Example 35

7-Pyridazinium methylene-10,11-ethylenedioxy-20(S)-camptothecin chloride (Compound 35)

The same procedure as Example 29, part (A), is used except that an equivalent amount of pyridazine is used in place of pyridine and an equivalent amount of 7-chloromethyl-10,11-ethylenedioxy-20(S)-camptothecin prepared in accordance with Example 14(A) is used in place of 7-chloromethyl-10,11-methylenedioxy-20(S)-camptothecin. Nominal Mass Spectrum M+: 499 mp: >282° C.

Example 36

7-(3'-Hydroxymethylpyridinium)methylene-10,11-ethylenedioxy-20(S)-camptothecin chloride (Compound 36)

The same procedure as Example 29, part (A), is used except that an equivalent amount of 3-hydroxymethylpyridine is used in place of pyridine and an equivalent amount of 7-chloromethyl-10,11-ethylenedioxy-20(S)-camptothecin, prepared according to Example 14(A) is used in place of 7-chloromethyl-10,11-methylenedioxy-20(S)-camptothecin. Nominal Mass Spectrum M+: 528 mp: >250° C. (d)

Example 37

7-(3'-Hydroxymethylpyridinium)methylene-10,11-methylenedioxy-20(S)-camptothecin chloride (Compound 37)

The same procedure as Example 29, part (A), is used except that an equivalent amount of 3-hydroxymethylpyridine is used in place of pyridine. Nominal Mass Spectrum M+: 514 mp: >230° C. (d).

Example 38

7-Pyrazinium methylene-10,11-ethylenedioxy-20(S)-camptothecin chloride (Compound 38)

The same procedure as Example 29, part (A), is used except that an equivalent amount of pyrazine is used in place of pyridine and an equivalent amount of 7-chloromethyl-10,11-ethylenedioxy-20(S)-camptothecin, prepared according to Example 14(A) is used in place of 7-chloromethyl-10,11-methy-lenedioxy-20(S)-camptothecin. Nominal Mass Spectrum M+: 499 mp: 298° C. (d)

Example 39

7-Pyrazinium methylene-10,11-methylenedioxy-20(S)-camptothecin chloride (Compound 39)

This compound is prepared by the procedure of Example 29, part (A), except that equivalent amount of pyrazine is used in place of pyridine. Nominal Mass Spectrum M+: 485 mp: 260° C. (d)

Example 40

7-imidazol-1-ylmethylene-10,11-methylenedioxy-20(S)-camptothecin (Compound 40)

The same procedure as Example 29, part (A), is used except that an equivalent amount of imidazole is used in place of pyridine. Nominal Mass Spectrum MH+: 473 mp: 222° C. (d)

Example 41

7-Imidazol-1-ylmethylene-10,11-ethylenedioxy-20(S)-camptothecin (Compound 41)

The same procedure as Example 29, part (A), is used except that an equivalent amount of imidazole is used in place of pyridine an equivalent amount of 7-chloromethyl-10,11-ethylenedioxy-20(S)-camptothecin, prepared according to Example 14(A), is used in place of 7-chloromethyl-10,11-methylenedioxy-20(S)-camptothecin. Nominal Mass Spectrum MH+: 487 mp: >325° C.

Example 42

7-(4'-Hydroxymethylpyridinium)methylene-10,11-ethylenedioxy-20(S)camptothecin chloride (Compound 42)

A procedure analogous to Example 36 was used except that an equivalent amount of 4-hydroxymethylpyridine was used. Nominal Mass Spectrum M+:527 mp: >260° C. (d)

Example 43

Pharmaceutical formulations

(A) Transdermal System

| Ingredients | Amount |
|---|---|
| Active compound | 600.0 mg |
| Silicone fluid | 450.0 mg |
| Colloidal silicone dioxide | 25.0 mg |

The silicone fluid and active compound are mixed together and the colloidal silicone dioxide is added with to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

(B) Oral Tablet

| Ingredients | Amount |
|---|---|
| Active compound | 200.0 mg |
| Starch | 20.0 mg |
| Magnesium Stearate | 1.0 mg |

The active compound and the starch are granulated with water and dried. Magnesium stearate is added to the dried granules and the mixture is thoroughly blended. The blended mixture is compressed into a tablet.

(C) Suppository

| Ingredients | Amount |
|---|---|
| Active compound | 150.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

(D) Injection

| Ingredients | Amount |
|---|---|
| Active Compound | 20.0 mg |
| Buffering Agents | q.s. |
| Propylene glycol | 0.4 |
| Water for injection | 0.6 mL |

The active compound and buffering agents are dissolved in the propylene glycol at about 50° C. The water for injection is then added with stirring and the resulting solution is filtered, filled into an ampule, sealed and sterilized by autoclaving.

(E) Capsule

| Ingredients | Amount |
|---|---|
| Active Compound | 200.0 mg |
| Lactose | 450.0 mg |
| Magnesium stearate | 5.0 mg |

The finely ground active compound is mixed with the lactose and stearate and packed into a gelatin capsule. Having described in invention in detail and by reference to preferred embodiments thereof, it will be apparent that modifications and variations are possible without departing from the scope of the invention defined in the appended claims.

What is claimed is:

1. A compound of formula (I)

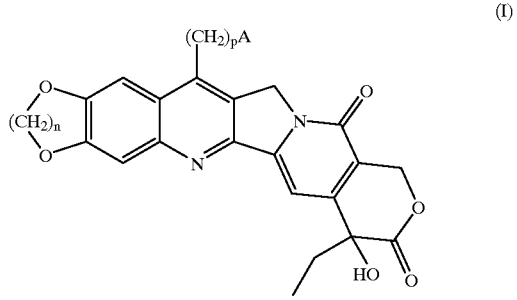

wherein A represents a moiety of the formula (IIA), (IIB) or (IIC):

(IIA)

(IIB)

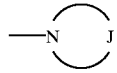

(IIC)

X is selected from the group consisting of alkyl, aryl, $(CH_2)_mOR^1$, $(CH_2)_mSR^1$ and $(CH_2)_mNR^1R^2$ wherein m is an integer of 0 to 6, and $R^1$ and $R^2$ are hydrogen, lower alkyl, aryl or together with the nitrogen form a 5–7 membered ring; q is an integer of 0 to 2; n represents the integer 1 or 2; p is an integer of 1 to 6; Y and W are selected from the group consisting of alkyl, aryl, alkoxy, aryloxy and amino, Q is oxygen or sulfur; P is phosphorus; J represents the atoms necessary to complete a 5 or 6 membered aromatic or substituted aromatic ring; and the pharmaceutically acceptable salts thereof.

2. A compound according claim 1 wherein p is 1, 2 or 3.
3. A compound according to claim 1 wherein p is 1.
4. A compound according to claim 1 wherein A represents —SX.
5. A compound according to claim 1 wherein A represents —SOX.
6. A compound according to claim I wherein A represents —SO₂X.

7. A compound according to claim 1 wherein X is selected from the group consisting of alkyl, aryl and $(CH_2)_m NR^1R^2$.

8. A compound according to claim 1 wherein A represents —POYW.

9. A compound according to claim 1 wherein A represents —PSYW.

10. A compound according to claim 1 wherein Q is oxygen and W and Y are both alkyl.

11. A compound according to claim 1 wherein J represents the atoms necessary to complete an aromatic ring selected from the group consisting of pyrazolyl, imidazolyl, triazolyl, oxazolyl, isoxazolyl, oxadiazolyl, thiazolyl, isothiazolyl, thiadiazolyl, pyridyl, pyrazinyl, pyrimidinyl, pyridazinyl, triazinyl and tetrazinyl.

12. A compound according to claim 1 wherein J represents the atoms necesary to complete an imidazolyl, pyridyl, pyridazinyl or pyrazinyl group.

13. A compound according to claim 1 wherein the aromatic ring completed by the atoms of J is substituted by one or more halogen, amino, dialkylamino, diphenylamino, alkyl, alkoxy, alkoxyalkyl, hydroxyalkyl, alkenyl, alkylthioalkyl, aminoalkyl, or —NHCONR$_2$ groups where R is hydrogen, alkyl, or aryl or two R groups may be combined to form together with the nitrogen atom a 3 to 7 membered heterocyclic ring.

14. A compound according to claim 1 wherein the aromatic ring completed by the atoms of J is unsubstituted or substituted by an alkyl or hydroxyalkyl group.

15. A compound according to claim 1 wherein J represents the atoms necessary to complete a pyridyl ring.

16. A compound according to claim 1 wherein J represents the atoms necessary to complete an imidazolyl ring.

17. A compound according to claim 1 wherein J represents the atoms necessary to complete a pyridazinyl ring.

18. A compound according to claim 1 wherein J represents the atoms necessary to complete a pyrazinyl ring.

19. The compound which is:

7-Methylthiomethyl-10,11-(ethylenedioxy)-20(S)-camptothecin;

7-Methylthiomethyl-10,11-(methylenedioxy)-20(S)-camptothecin;

7-(2-Pyridylthio)methyl-10,11-(ethylenedioxy)-20(S)-camptothecin;

7-(2-Pyridylthio)methyl-10,11-(methylenedioxy)-20(S)-camptothecin;

7-(2-Pyrimidylthio)methyl-10,11-(methylenedioxy)-20(S)-camptothecin;

7-(4-Nitrophenylthio)methyl-10,11-(methylenedioxy)-20(S)-camptothecin;

7-(4-Acetamidophenylthio)methyl-10,11-(methylenedioxy)-20(S)-camptothecin;

7-Methylsulfinylmethyl-10,11-(ethylenedioxy)-20(S)-camptothecin;

7-Methylsulfinylmethyl-10,11-(methylenedioxy)-20(S)-camptothecin;

7-(2-Pyridylsulfinyl)methyl-10,11-(methylenedioxy-20(S)-camptothecin;

7-Methylsulfonylmethyl-10,11-(ethylenedioxy)-20(S)-camptothecin;

7-Methylsulfonylmethyl-10,11-(methylenedioxy)-20(S)-camptothecin;

7-Dimethylphosphonomethylene-10,11(methylenedioxy)-20(S)-camptothecin;

7-Dimethylphosphonomethylene-10,11-(ethylenedioxy)-20(S)-camptothecin;

7-Di-n-butylphosphonomethylene-10,11-(ethylenedioxy)-20(S)-camptothecin;

7-(4-Aminophenylthio)methyl-10,11-(methylenedioxy)-20(S)-camptothecin;

7-(4-Acetamidophenylthio)methyl-10,11-(ethylenedioxy)-20(S)-camptothecin;

7-(4-Aminophenylthio)methyl-10,11-(ethylenedioxy)-20(S)-camptothecin;

7-(2-Aminoethylthio)methyl-10,11-(ethylenedioxy)-20(S)-camptothecin;

7-(2-Dimethylaminoethylthio)methyl-10,11-(ethylenedioxy)-20(S)-camptothecin;

7-(3-Aminopropylthio)methyl-10,11-(ethylenedioxy)-20(S)-camptothecin;

7-(3-Dimethylaminopropylthio)methyl-10,11-(ethylenedioxy)-20(S)-camptothecin;

7-(2-Methylaminoethylthio)methyl-10,11-(ethylenedioxy)-20(S)-camptothecin;

7-(2-Aminoethylthio)methyl-10,11-(methylenedioxy)-20(S)-camptothecin;

7-(2-Methylaminoethylsulfinyl)methyl-10,11-(ethylenedioxy)-20(S)-camptothecin;

7-(3-Aminopropylsulfinyl)methyl-10,11-(ethylenedioxy)-20(S)-camptothecin;

7-(3-Dimethylaminopropylsulfinyl)methyl-10,11-(ethylenedioxy)-20(S)-camptothecin;

7-(4-(2-Dimethylaminoacetamido)phenylthio)methyl-10,11-(ethylenedioxy)-20(S)-camptothecin;

7-Pyridinium methylene-10,11-methylenedioxy-20(S)-camptothecin;

7-Pyridinium methylene-10,11-ethylenedioxy-20(S)-camptothecin;

7-Pyridinium methylene-10,11-ethylenedioxy-20(R,S)-camptothecin;

7-(3'-Methylimidazolium)methylene-10,11-ethylenedioxy-20(S)-camptothecin;

7-(3'-Methylimidazolium)methylene-10,11-methylenedioxy-20(S)-camptothecin;

7-Pyridazinium methylene-10,11-methylenedioxy-20(S)-camptothecin;

7-Pyridazinium methylene-10,11-ethylenedioxy-20(S)-camptothecin;

7-(3'-Hydroxymethylpyridinium)methylene-10,11-ethylenedioxy-20(S)-camptothecin;

7-(3'-Hydroxymethylpyridinium)methylene-10,11-methylenedioxy-20(S)-camptothecin;

7-Pyrazinium methylene-10,11-ethylenedioxy-20(S)-camptothecin;

7-Pyrazinium methylene-10,11-methylenedioxy-20(S)-camptothecin;

7-Imidazol-1-ylmethylene-10,11-methylenedioxy-20(S)-camptothecin;

7-Imidazol-1-ylmethylene-10,11-ethylenedioxy-20(S)-camptothecin; or 7-(4'-Hydroxymethylpyridinium)methylene-10,11-ethylenedioxy-20(S) camptothecin;

and pharmaceutically acceptable salts thereof.

20. A compound according to claim 1 in the R configuration.

21. A compound according to claim 1 in the S configuration.

22. A pharmaceutical composition comprising a compound of claim 1 and a pharmaceutically acceptable carrier.

23. A method of inhibiting topoisomerase I enzyme comprising contacting said enzyme with an effective topoisomerase I inhibitory amount of a compound of claim 1.

24. A method of treating a tumor in a mammal comprising administering to said mammal, an antitumor effective amount of a compound of claim 1.

25. A process for preparing a compound of formula (I) as defined in claim 1 or a pharmaceutically acceptable salt thereof which comprises:

(A) for the preparation of compounds of formula (I) wherein A is —SX reacting a compound of the formula (VI)

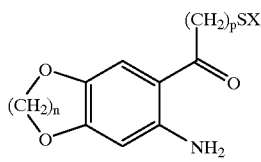

(VI)

wherein X is alkyl, aryl, $(CH_2)_mOR^1$, $(CH_2)_mSR^1$, or $(CH_2)_mNR^1R^2$ or a protected derivative thereof, with a compound of the formula (VII)

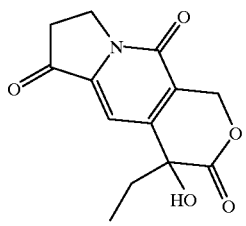

(VII)

or (B) for the preparation of compounds of formula (I) wherein A is $S(CH_2)_mNH_2$, hydrolysing a compound of formula (IB)

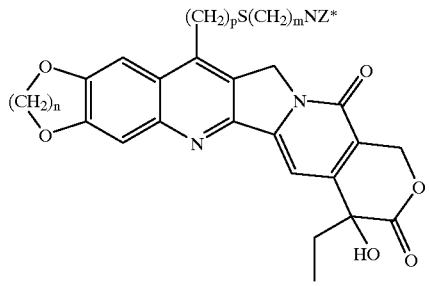

I-B wherein Z* is a protective group; or (C) for the preparation of compounds of formula (I) wherein A is a moiety of formula (IIB) or (IIC), reacting a compound of formula (XII)

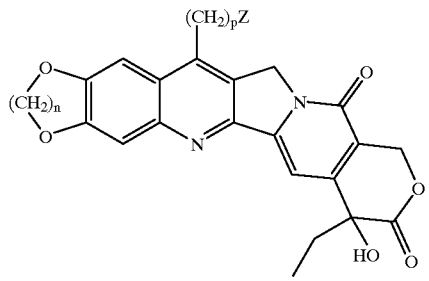

(XII)

wherein Z is a leaving group with a suitable nucleophile;

and if necessary and/or desired subjecting the compound thus obtained to one or more further reactions comprising:

(i) converting the resulting compound of formula (I) or a salt or a protected derivative thereof into another compound of formula (I) and/or (ii) removing any protecting group or groups and/or (iii) converting a compound of formula (I) or a salt thereof into a physiologically acceptable salt thereof.

26. A process according to claim 25 for the preparation of a compound of formula (I) wherein A is a moiety of formula (IIC) which comprises reacting a compound of formula (XII)

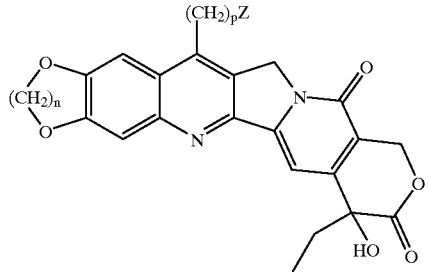

(XII)

with a nucleophile of formula (III)

(III)

in a melt of the nucleophile in the absence of a solvent.

27. A process according to claim 25 for the preparation of a compound of formula (I) wherein A is a moiety of formula (IIB) which comprises reacting a compound of formula (XII)

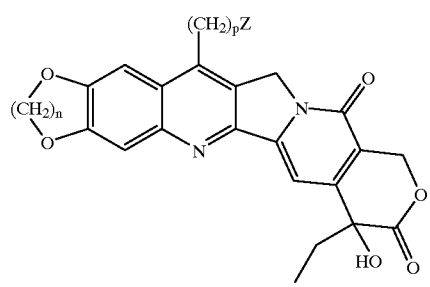 (XII)
with a compound of formula (XIII)
RPWY  (XIII)
wherein R is a group of formula QR* and R* is a readily displaceable group, in the presence of a solvent.
28. A process as claimed in claim 27 wherein the compound of formula (XIII) is a trialkyl or triacyl phosphite.
* * * * *